(12) United States Patent
Ross, III et al.

(10) Patent No.: US 6,246,062 B1
(45) Date of Patent: Jun. 12, 2001

(54) MISSING LENS DETECTION SYSTEM AND METHOD

(75) Inventors: Denwood F. Ross, III; Timothy P. Newton, both of Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 09/187,579

(22) Filed: Nov. 5, 1998

(51) Int. Cl.[7] .................................................. G01N 21/64
(52) U.S. Cl. ............................................... 250/461.1
(58) Field of Search .......................................... 250/461.1

(56) References Cited

U.S. PATENT DOCUMENTS

| | | |
|---|---|---|
| 3,666,885 | 5/1972 | Hemsley et al. . |
| 3,692,985 | 9/1972 | Kalman . |
| 3,770,969 | 11/1973 | Ansevin et al. . |
| 3,820,899 | 6/1974 | McCormack . |
| 3,904,294 | 9/1975 | Gold et al. . |
| 3,988,068 | 10/1976 | Sprague . |
| 4,002,823 | 1/1977 | Van Oosterhout . |
| 4,158,502 | 6/1979 | Greiner et al. . |
| 4,162,126 | 7/1979 | Nakagawa et al. . |
| 4,209,252 | 6/1980 | Arditty et al. . |
| 4,317,613 | 3/1982 | Grosser . |
| 4,519,041 | 5/1985 | Fant et al. . |
| 4,553,847 | 11/1985 | Lang . |
| 4,691,231 | 9/1987 | Fitzmorris et al. . |
| 4,733,360 | 3/1988 | Kobayashi et al. . |
| 4,815,844 | 3/1989 | Schmalfuss et al. . |
| 4,817,166 | 3/1989 | Gonzalez et al. . |
| 4,825,263 | 4/1989 | Desjardins et al. . |
| 5,039,459 | 8/1991 | Kindt-Larsen et al. . |
| 5,066,120 | 11/1991 | Betrand . |
| 5,068,799 | 11/1991 | Jarrett, Jr. . |
| 5,080,839 | 1/1992 | Kindt-Larsen . |
| 5,081,685 | 1/1992 | Jones, III et al. . |
| 5,091,963 | 2/1992 | Litt et al. . |
| 5,094,609 | 3/1992 | Kindt-Larsen . |
| 5,123,735 | 6/1992 | Hegarty . |
| 5,164,462 | 11/1992 | Yang . |
| 5,249,029 | 9/1993 | Sommer et al. . |
| 5,260,576 | 11/1993 | Sommer, Jr. et al. ............. 250/359.1 |
| 5,268,735 | 12/1993 | Hayashi . |
| 5,399,692 | 3/1995 | Hung et al. . |
| 5,466,768 | 11/1995 | Yang . |
| 5,500,024 | 3/1996 | Hung et al. . |
| 5,500,732 | 3/1996 | Ebel et al. . |
| 5,528,878 | 6/1996 | Edwards et al. . |
| 5,568,715 | 10/1996 | Ebel et al. . |
| 5,574,554 | 11/1996 | Su et al. . |
| 5,578,331 | 11/1996 | Martin et al. . |
| 5,626,000 | 5/1997 | Edwards et al. . |
| 5,633,504 | 5/1997 | Collins et al. ..................... 250/461.1 |
| 5,640,464 | * 6/1997 | Ebel et al. ........................... 382/143 |
| 5,649,410 | 7/1997 | Martin et al. . |
| 5,675,962 | 10/1997 | Martin et al. . |
| 5,687,541 | 11/1997 | Martin et al. . |
| 5,706,634 | 1/1998 | Edwards et al. . |
| 5,745,230 | 4/1998 | Edwards et al. . |
| 5,749,205 | 5/1998 | Edwards et al. . |

FOREIGN PATENT DOCUMENTS

| | | |
|---|---|---|
| 2057832 | 6/1992 | (CA) . |
| 0 063 761 A1 | 11/1982 | (DE) . |
| 3432002 C2 | 11/1987 | (DE) . |
| 0 491 663 A1 | 6/1992 | (DE) . |
| 2 433 767 | 3/1980 | (FR) . |
| 2 171 812 | 9/1986 | (GB) . |
| 59-108934 | 6/1984 | (JP) . |
| 59-160734 | 9/1984 | (JP) . |
| 2 257007 | 10/1990 | (JP) . |

* cited by examiner

Primary Examiner—Constantine Hannaher
(74) Attorney, Agent, or Firm—Anne B. Kiernan

(57) ABSTRACT

A system for determining the presence and optionally the position of an ophthalmic product such as a contact lens in a container.

24 Claims, 4 Drawing Sheets

MISSING LENS DETECTION SYSTEM AND METHOD

FIELD OF THE INVENTION

The present invention relates generally to systems for detecting the presence and optionally the position of a product within a container or package, and more particularly, to an apparatus and method for verifying the presence in the container of an ophthalmic product such as a contact lens.

BACKGROUND OF THE INVENTION

Automated systems are used for producing ophthalmic lenses as disclosed in U.S. Pat. No. 5,080,839. These systems have achieved a very high degree of automation and enable lenses to be molded, removed from the molds, further processed and subsequently packaged, all without any direct human involvement. Even with highly automated systems, however, it has been necessary for each package to be checked visually by personnel to verify that the package contained a lens. These arrangements have increased manpower requirements and the associated labor costs. Automated loading of lenses without verifying an actual transfer of a contact lens into a package can result in more than two percent of processed packages being shipped without a lens. This is more than ten times the average rate found on one production line which uses manual loading of lenses.

In one prior art system disclosed in U.S. Pat. No. 5,568,715, detection of a lens in a package is accomplished by backlighting the package with diffuse light and performing an optical inspection with a video camera. In this system, the package is illuminated from the bottom and a camera module disposed over the package takes a picture of the package. The image is processed by a computerized image processing system to determine whether the lens is missing from the package. While this approach works relatively well, it is expensive and software intensive.

U.S. Pat. No. 5,633,504 discloses a system and method for inspecting a hydrated contact lens by illuminating the lens and photographing with a camera the flourescent light generated in the lens or in some portion of the receptacle and blocked by the lens. In the preferred method, the lens is provided with an ultraviolet absorbing medium. In one embodiment, light having certain wavelengths will induce fluorescence in the lens and cause the lens to appear as a bright area against a dark field. Defects in the lens appear darker than the surrounding areas. In another embodiment, a part of the lens holding receptacle or support is made to fluoresce by exposure to light having wavelengths outside of the range of wavelengths used by the camera. These wavelengths do not cause lens fluorescence such that defects appear as light areas within the lens.

Accordingly, there exists a need for a new type of lens detection system which provides low cost detection with high accuracy. The detection system may be used as part of an automated detection system which includes a transport and ejector conveyor for ejecting any defective packages which the automated detection system determines are missing lenses in the packages.

SUMMARY OF THE INVENTION

It is a primary object of the present invention to provide a system and a method for verifying the presence and optionally the presence and position of an ophthalmic product disposed in the package by directing electromagnetic radiation at the product/package combination.

It is another object of the present invention to provide a system for verifying the presence or absence of an ophthalmic product disposed in the package which provides an accuracy of detection greater than 1 in 1,000,000.

It is still another object of the present invention to provide a system for verifying the presence or absence of an ophthalmic product disposed in a package which is economical to manufacture and use.

In accordance with the above objects and additional objects that will become apparent hereinafter, the present invention provides a system for determining the presence and optionally the position of an ophthalmic product such as a contact lens in a container. The lens will fluoresce, absorb or reflect, preferably absorb or reflect, most preferably absorb, electromagnetic radiation in a different amount than the container. This difference may be due to a media included in the lens which reacts differently to electromagnetic energy in a specified wavelength range than does the container. The container includes a receptacle for the lens and may be constructed from a material which is substantially transparent to electromagnetic energy in the specified wavelength range. The detection system includes an apparatus for detecting the presence and optionally the position of an ophthalmic product in a container, comprising:

a) a source of electromagnetic energy located relative to the container to direct electromagnetic energy at the container, b) a detector disposed relative to the container and the source to detect electromagnetic energy from the source which passes through or is reflected by the product and the container; and c) means for indicating the presence or position of the product in the container responsive to absorption, reflection or fluorescence of the electromagnetic energy by the product.

The present invention also provides a method for detecting the presence or presence and position of an ophthalmic product in a container, the product including a media which absorbs or reflects electromagnetic energy of a frequency in a specified range, the method comprising:

a) directing electromagnetic energy at the product and the container, b) detecting the electromagnetic energy which passes through or is reflected by the product and the container; and c) processing the detected electromagnetic energy to determine the presence or position of the product in the container.

The present invention provides a relatively simple and economical system for determining the presence and optionally the position of an ophthalmic product in a container. It does not comprise a vision system, nor complicated software which does pixel-by-pixel analysis of an image.

BRIEF DESCRIPTION OF THE DRAWINGS

The present invention will now be described with particular reference to the accompanying drawings.

DETAILED DESCRIPTION OF THE PREFERRED EMBODIMENTS

Figure 1:
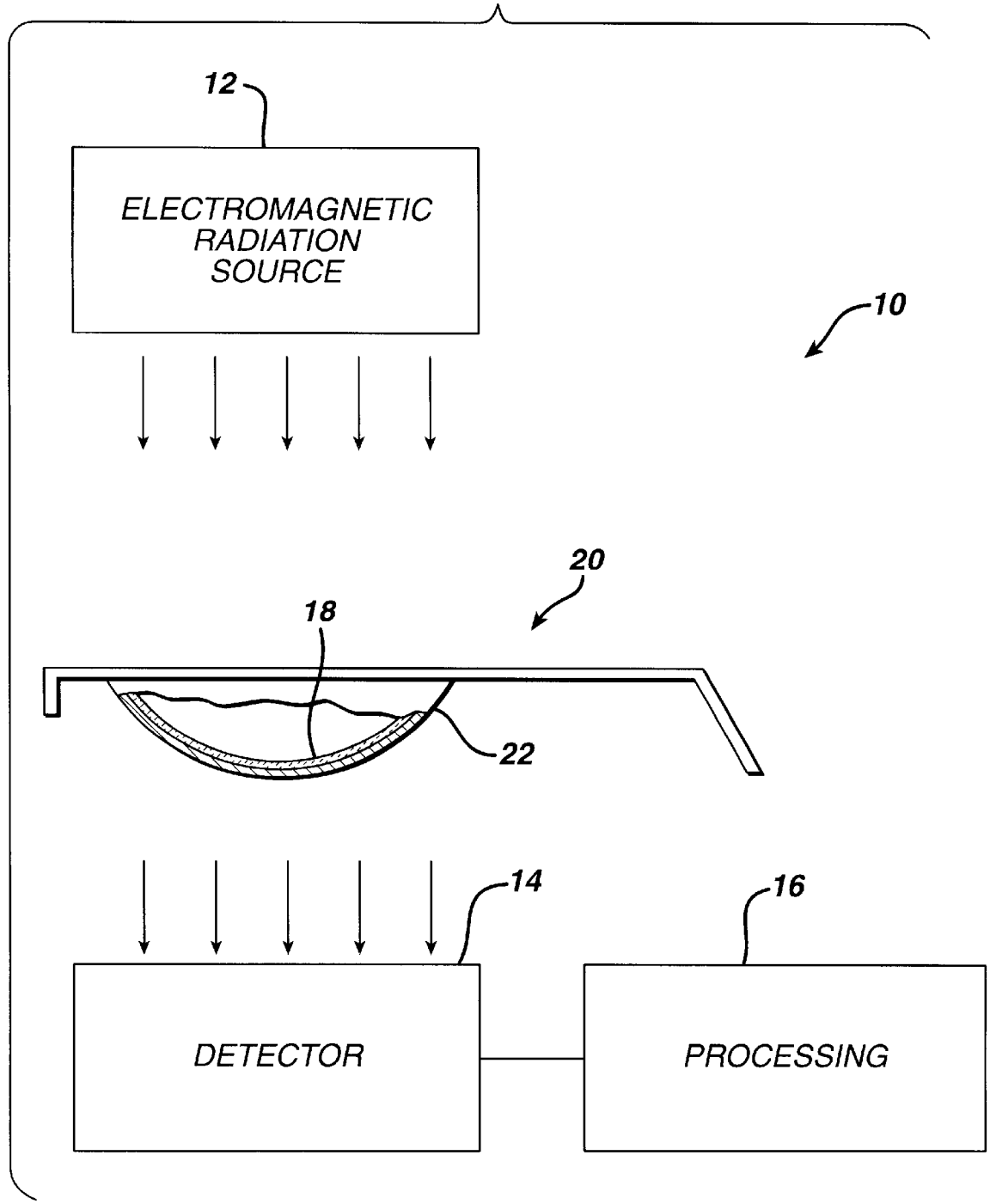
FIG. 1 is a schematic of a missing lens detection system in accordance with the present invention.

Referring now to the several figures of the drawings, there is depicted a missing lens detection system generally characterized by the reference numeral 10. Referring to FIG. 1, the detection system 10 comprises an electromagnetic radiation source 12 and a detector 14. The source 12 can be a broad-band source which produces ultraviolet light, visible light, and infrared light. For example, a visible light source will produce a portion of the electromagnetic radiation in the ultraviolet band. Alternatively, the source 12 can generate electromagnetic radiation in a narrow band, e.g., ultraviolet (a wavelength or range of wavelengths within about 190 to 400 nanometers). In yet another embodiment, the source 12 can produce electromagnetic radiation in a selected group of ranges such as the ultraviolet and visible bands. Similarly, the detector 14 may be responsive to wavelengths of radiation in a particular range, or it may be responsive to broad bands and/or used in combination with a filter to detect a specified range of interest. The detector 14 may be a spectrometer or calorimeter. These components are commercially available units and need not be described in specific detail herein. In an illustrative embodiment, source 12 may utilize a Phillips light bulb P/NPL-S 9W/10, which is a regular visible light source which produces some electromagnetic energy in the ultraviolet band. In accordance with the invention, a source 12 which produces electromagnetic energy in a broad band can be used with a detector 14 adapted to sense for a limited range. Alternatively, the source 12 can produce a limited range of wavelengths, or both the source 12 and detector 14 can operate in the same band. There can be more than one source and more than one detector, preferably less than four detectors or sensors, however one of each is preferred. The detector detects the electromagnetic radiation and does not create an image based on the detected electromagnetic radiation. Preferably the detector has a diameter of approximately 1 millimeter or thereabouts, and measures a total electromagnetic radiation sensed over the area of the detector. An exemplary detector 14 is Part No. US 365 HFI-010.00, available from Electronic Instrumentation Technology Inc., in Sterling Va. The EIT detector has a sensitivity for radiation having a wavelength of 365 nanometers. The detector 14 communicates with differential signal processing 16 to provide an indication of the presence and optionally the position of an ophthalmic product 18, e.g., a lens, in a carrier or container 20. Preferably the system is calibrated so that the ratio of the energy detected when the lens 18 is absent from the container 20 to the energy detected when the lens 18 is present in the container 20 is at least 1.1:1. This ratio is preferably more than 1.5:1 and most preferably greater than 2:1. The detector 14 is sensitive to a limited number of wavelengths or range of wavelengths. For example the detector may be sensitive to a bandwidth of 200 nanometers or less, e.g. from 200 to 400 nanometers, preferably less than 50 nanometers and most preferably less than 25 nanometers, with the preferred embodiment having a sensitivity of one nanometer. Preferably, the detector sends a single energy output to the processing circuit which is compared to a standard. The electrical processing circuit is calibrated to operate with a range of limited voltages, for example, an 8V signal would be the highest voltage indicative of the absence of the lens 18 in the package, and a 3V signal indicative of the presence of the lens 18 in the package. The voltage signal could go to zero volts if the lens blocks all the UV radiation. A predetermined limit can be established, such as when the sensed radiation results in a signal greater than 5V, to indicate the absence of the lens 18 from the package. Similarly, the detector 14 can be calibrated to indicate whether the lens 18 is oriented properly in the container 20. If the lens 18 is not disposed in the proper orientation, such as, for example, along the sides of the container receptacle or bowl described below, the quantity of electromagnetic energy which is absorbed or reflected back to the detector 14 may be less than the threshold value which indicates when the lens 18 is properly positioned. This information is then communicated to a controller to reject or accept a package as described below.

Figure 2:
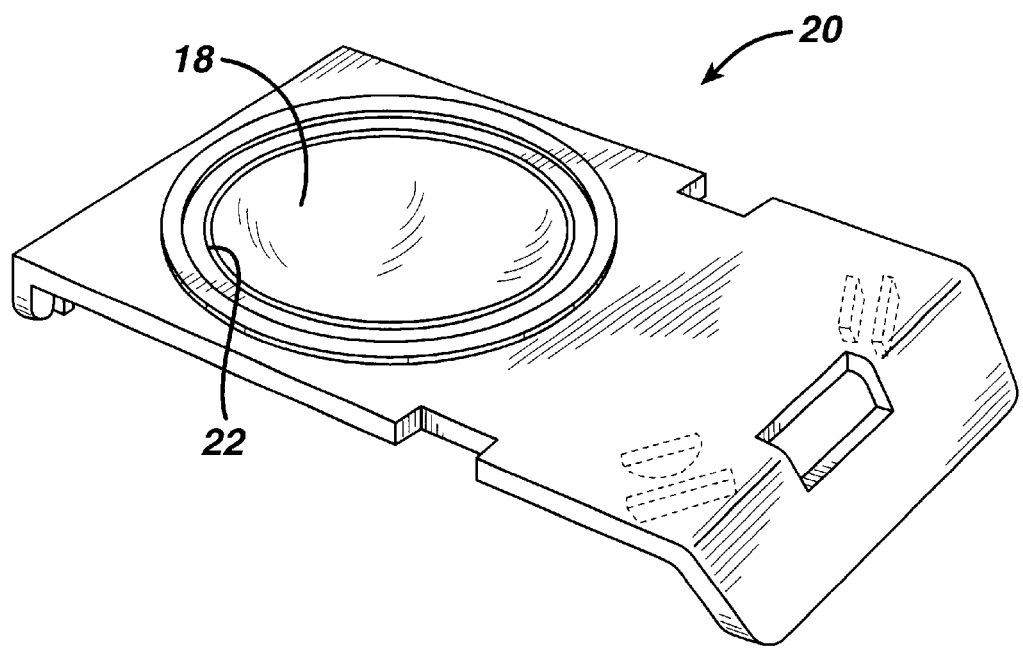
FIG. 2 is an isometric view of a container and lens disposed therein.
Figure 3:
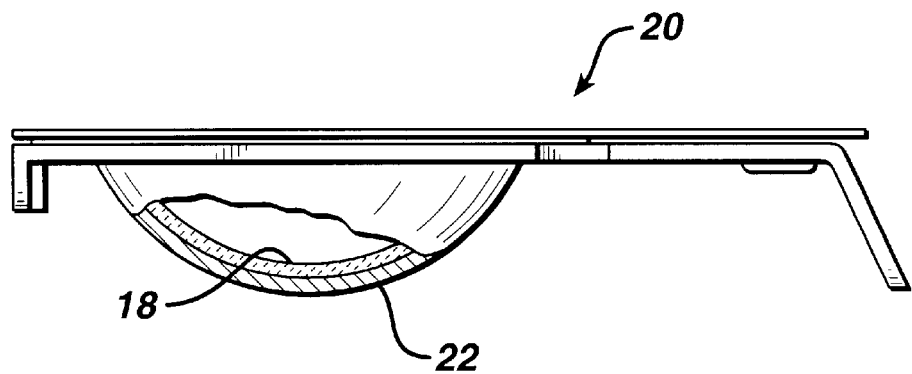
FIG. 3 is a side elevational view of the container and lens of FIG. 2.
Figure 5:
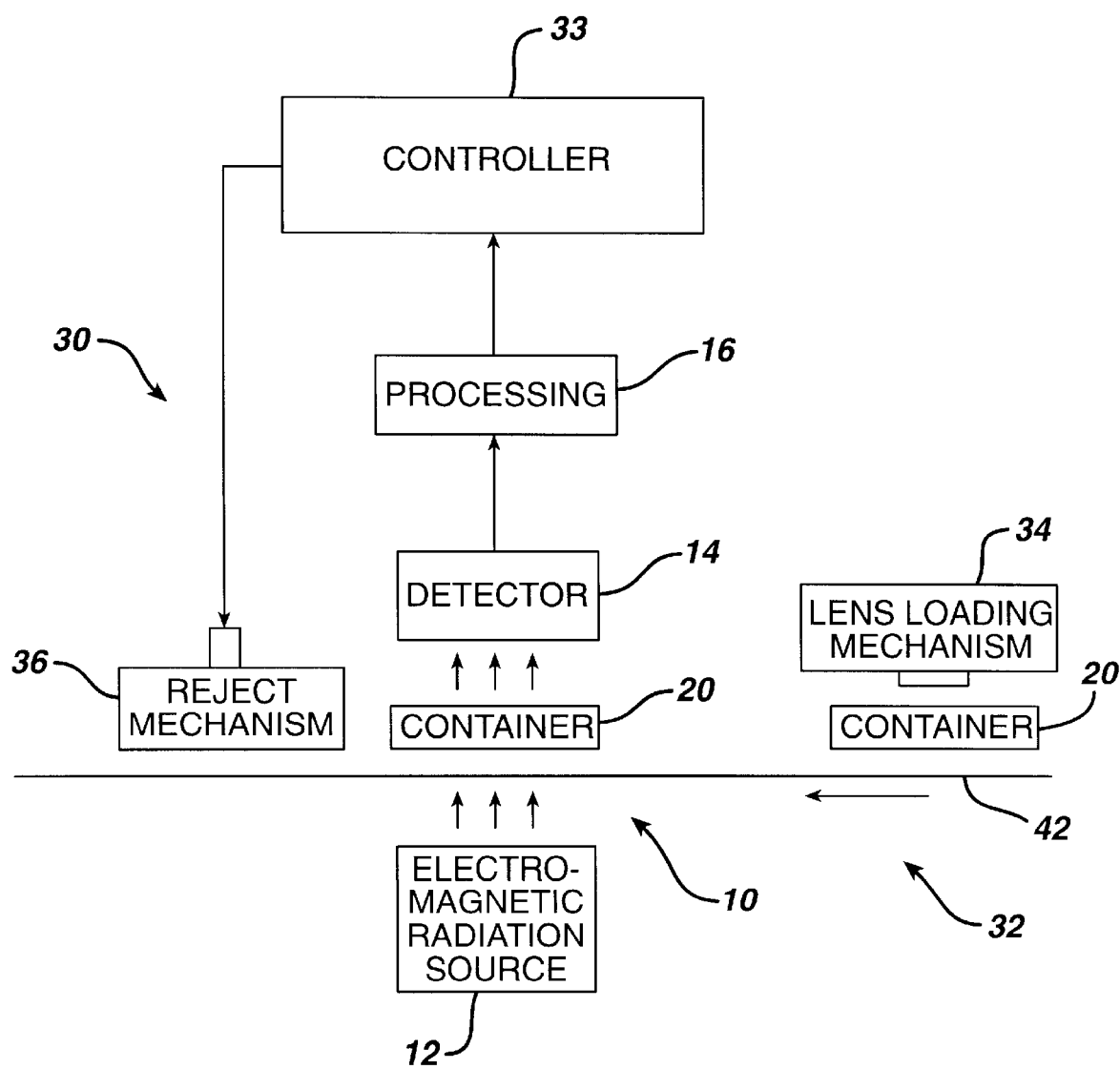
FIG. 5 is a schematic of an automated system for detecting a missing lens in accordance with the present invention.

The lens 18 is disposed within a receptacle or bowl 22 of the container 20 in a conventional manner as shown in FIGS. 2 and 3. The container 20 has a substantially planar top surface and the bowl is generally concave when viewed from the top of the container. The lens 18 is located in the bowl 22, and preferably, it is not immersed in liquid. Alternatively, the lens 18 can be fully submerged in a saline solution. The source 12 and detector 14 are disposed relative to the container 20 such that electromagnetic radiation is directed at the bowl 22 of the container 20 as shown in FIG. 5. Preferably the container 20 has no lidstock. However, the invention can work with either a transmissive or reflective lidstock. If a reflective lidstock is used, the source 12 and detector 14 can both be located on the bowl 22 and the lens 18 side of the container 20.

The presence or position of the lens 19 within the bowl 22 is a function of the absorption of electromagnetic radiation passing through or reflecting from the lens 18 and container 20. The preferred contact lenses 18 used with the present invention contain an ultraviolet blocker which absorbs approximately 94% of UV a and b rays. An exemplary lens material is available under the tradename Etafilcon A with Norbloc™ as the UV blocker. These lenses are commercially available under the tradename Surevue™ and Acuvue™ from Johnson & Johnson Vision Products, Inc., Jacksonville, Fla. Fabrication of a UV absorbing lens is known in the art as disclosed in, for example, U.S. Pat. No. 5,399,692, the disclosure of which is hereby incorporated by reference. Other patents which disclose contact lenses which absorb UV radiation include U.S. Pat. Nos. 4,390,676 and 4,528,311. UV light may also be absorbed by a UV photoinitiator.

The surrounding container material is selected so as to not appreciably absorb and block ultraviolet radiation to the same degree as the lens. Specifically, the plastic in the container 20 must not absorb and block the electromagnetic radiation in the range sensitive to detection by detector 14, i.e., 365 nanometers, to the same degree as the lens 18. Exemplary plastic materials which may be used for the container 20 include, but are not limited to, polypropylene and polystyrene. Thus, the presence or position of the lens 18 within the container 20 can be determined by comparing the level of electromagnetic radiation received by the detector in the specified spectral range, for example, ultraviolet, with a known level for the container 20 alone. The processing circuitry 16 can provide a signal indicative of the presence or absence of the lens 18 based on the reduced electromagnetic radiation received by the detector.

In another embodiment, the source 12 can emit electromagnetic radiation in the infrared range. The presence of a lens 18 is indicated by a reduced level of infrared radiation at the detector 14 as compared to a baseline infrared level associated with an empty container 20. The package preferably includes a fluid such as an aqueous solution to facilitate transmitting infrared radiation from the package to the lens 18. The amount of aqueous solution in the container 20 can be just enough to wet the surfaces of the lens 18. The lens 19 is an infrared blocker at certain wavelengths to which the detector 14 is sensitive. Testing has demonstrated good results using this method, although not as good as with the UV range. It is also possible to utilize electromagnetic radiation in the visible spectral range. With this embodiment, a tinted lens 18 can be employed whereby the tinted lens absorbs and blocks electromagnetic energy in the visible spectrum to which the detector 14 is sensitive. Similarly, lens 18 may be more hygroscopic than the container 20. Therefore due to the presence of water, the lens may absorb or reflect the electromagnetic energy to a different degree than the container.

Figure 4:
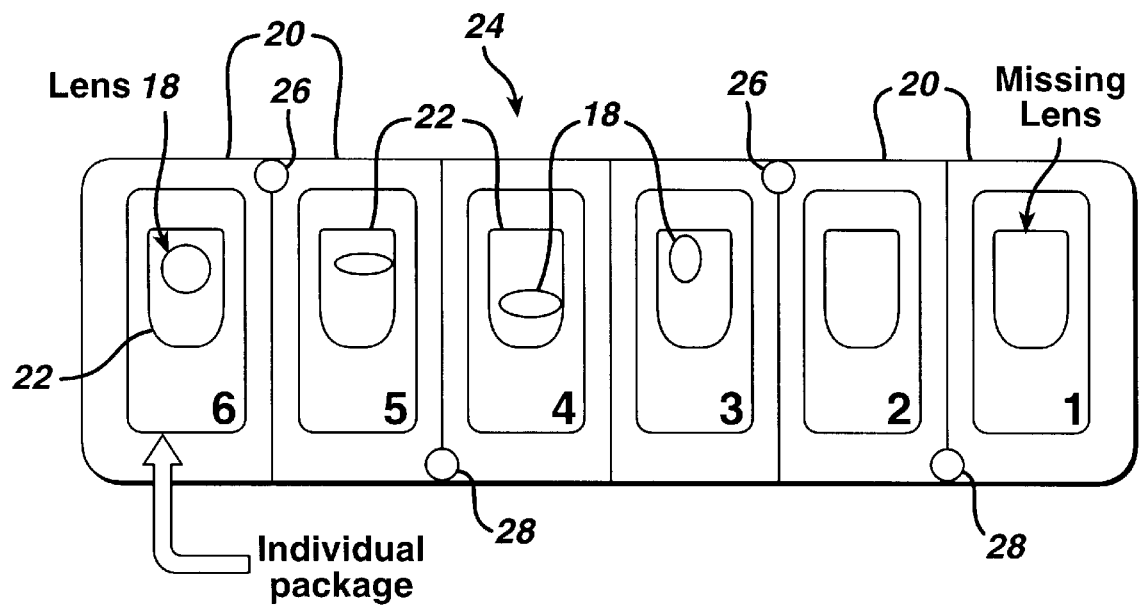
FIG. 4 is a top plan view schematic of an array of containers.

Referring now to FIG. 4, there is depicted a schematic top planar view of a blister package 24 comprising a linear array of six individual containers 20, each of which is to be checked by the automated detection system to determine if each individual container has a lens 18 disposed in bowl 22. The containers 20 define first alignment lugs 26 depending from a first side of the container adjacent to and slightly spaced from the bowl 22, and second alignment lugs 28 depending from a second side of the container 20. If any lenses 18 are missing, the entire blister pack is rejected. Alternatively and preferably, the lenses 18 are contained in individual containers 20, at the time of detection, so that a missing lens 18 in a particular container 20 does not result in rejection of an entire group of containers 24.

FIG. 5 is a schematic illustration of a lensload system 30 employing an automated detection system having a transport and ejector assembly. Details of a lensload system are disclosed in U.S. Pat. No. 5,568,715, the disclosure of which is hereby incorporated by reference. The system 30 generally comprises a transport subsystem 32, a missing lens detector 10, and a controller 33. The lenses are transferred by a lens loading mechanism or assembly 34 which loads the lenses 18 into the containers 20. The containers 20 are conveyed via a conveyor 42 in the direction of the arrow to the missing lens detector 10. The radiation from the electromagnetic radiation source 12 is directed as indicated by the arrows at and through the container 20 as shown. The radiation detector 14 measures the radiation which impinges on it, and the processing circuitry 16 of the detector communicates the amount of radiation measured to the controller 33. The controller 33 is coupled to the reject mechanism 36. The reject mechanism 36, shown as a push-bar, under the control of the controller 33 removes those containers 20 which are missing lenses 18. Containers 20 that do not have a detected lens are pushed by a push bar 44 to another conveyor (not shown) which delivers them to a trash bin.

In the preferred embodiment, detection is performed after hydration, and after transfer of the lens to the bowl of the final container, but before the addition of the saline solution and placement and attachment of the lidstock to the bowl of the container. The detection step is preferably after the inspection step, which uses a vision system and complicated software which occurs before the hydration step.

All patents, publications, applications, and test methods mentioned herein are incorporated by reference.

Many variations of the present invention will suggest themselves to those skilled in the art in light of the above detailed description. All such obvious variations are within the full intended scope of the appended claims.

What is claimed is:

1. An apparatus for detecting the presence or position of an ophthalmic product in a container, comprising:

a) source of electromagnetic energy located relative to the container to direct electromagnetic energy at the container;
 b) a non-imaging detector disposed relative to the container and the source to detect electromagnetic energy from the source which passes through or is reflected by the product and the container; and
 c) means for indicating the presence or position of the product in the container responsive to fluorescence, absorption or reflection of the electromagnetic energy by the product.

2. An apparatus as defined in claim 1, wherein the product is a contact lens.

3. An apparatus as defined in claim 2, wherein the source emits electromagnetic energy having a wavelength in the ultraviolet range.

4. An apparatus as defined in claim 2, wherein the source emits electromagnetic energy having a wavelength in the infrared range.

5. An apparatus as defined in claim 2, wherein the contact lens contains an ultraviolet absorbing media which absorbs electromagnetic energy in the ultraviolet range.

6. An apparatus as defined in claim 5, wherein said absorbing media is an ultraviolet blocker.

7. An apparatus as defined in claim 5, wherein said absorbing media is an ultraviolet photoinitiator.

8. An apparatus as defined in claim 2, wherein the source emits electromagnetic energy in the visible range and said contact lens contains a tint.

9. An apparatus as defined in claim 2, wherein the lens is a hygroscopic lens.

10. An apparatus as defined in claim 2, wherein the lens includes a media which absorbs or reflects electromagnetic energy of a wavelength in a specified range, and the container includes a receptacle for the lens and is constructed from a material which absorbs or reflects the electromagnetic energy differently than the lens.

11. An apparatus as defined in claim 2, wherein said lens includes a media which absorbs or reflects electromagnetic energy having a wavelength in a specified range and said detector is sensitive to electromagnetic radiation in the specified range.

12. An apparatus as defined in claim 2, further comprising a plurality of sources and a plurality of detectors disposed relative to each other for detecting the presence or position of a contact lens in a container.

13. An apparatus as defined in claim 2, wherein the source emits electromagnetic energy having a wavelength in the ultraviolet range, and said detector is sensitive to the electromagnetic energy in the ultraviolet range.

14. An apparatus as defined in claim 2, wherein the source emits electromagnetic energy having a wavelength in the ultraviolet range, and the detector is sensitive to the electromagnetic energy in the ultraviolet range, and the contact lens absorbs electromagnetic energy having a wavelength in the ultraviolet range.

15. An apparatus as recited in claim 1, wherein said detector is a calorimeter.

16. The apparatus as recited in claim 15, further comprising a filter.

17. The apparatus recited in claim 1, further comprising a filter.

18. The apparatus as recited in claim 17, further comprising a filter.

19. A method for detecting the presence or position of an ophthalmic product in a container, the product including a media which fluoresces, absorbs or reflects electromagnetic energy of a frequency in a specified range, the method comprising:

(a) directing electromagnetic energy of a frequency in the specified range at the product and the container;

(b) detecting, without imaging, the electromagnetic energy which passes through or is reflected by the product and the container; and (c) processing the detected electromagnetic energy to determine the presence or position of the product in the container.

20. A method as defined in claim 19, wherein the electromagnetic radiation is in the ultraviolet range.

21. A method as defined in claim 19, wherein the electromagnetic radiation is in the infrared range.

22. A method for detecting the presence or position of an ophthalmic product in a container, the product including a media which fluoresces, absorbs or reflects the electromagnetic energy of a frequency in a specified range, the method comprising:

(a) directing electromagnetic energy at the product and the container;

(b) detecting, without imaging, the absence of or reduction in electromagnetic energy of a frequency in a specified range which passes through or is reflected by the product and the container; and (c) processing the detected electromagnetic energy to determine the presence or position of the product in the container.

23. A method as defined in claim 22, wherein the electromagnetic radiation is in the ultraviolet range.

24. A method as defined in claim 22, wherein the electromagnetic radiation is in the infrared range.

* * * * *

UNITED STATES PATENT AND TRADEMARK OFFICE
CERTIFICATE OF CORRECTION

PATENT NO.    : 6,246,062 B1
DATED         : June 12, 2001
INVENTOR(S)   : Denwood F. Ross, III and Timothy P. Newton It is certified that error appears in the above-identified patent and that said Letters Patent is hereby corrected as shown below:

Column 6,
Line 59, delete "further comprising a filter" and replace therefor:
-- wherein said detector is a spectrometer --.

Signed and Sealed this

Eighteenth Day of November, 2003

JAMES E. ROGAN
*Director of the United States Patent and Trademark Office*